United States Patent [19]

Engelhardt et al.

[11] Patent Number: 5,331,059
[45] Date of Patent: * Jul. 19, 1994

[54] HYDROPHILIC, HIGHLY SWELLABLE HYDROGELS

[75] Inventors: Friedrich Engelhardt, Frankfurt am Main; Rüdiger Funk, Wiesbaden-Naurod; Ulrich Riegel, Frankfurt am Main; Gerlinde Ebert, Dreieich; Hanss-Jerg Kleiner, Kronberg, all of Fed. Rep. of Germany

[73] Assignee: Cassella Aktiengesellschaft, Frankfurt, Fed. Rep. of Germany

[ * ] Notice: The portion of the term of this patent subsequent to Dec. 28, 2010 has been disclaimed.

[21] Appl. No.: 974,621

[22] Filed: Nov. 12, 1992

[30] Foreign Application Priority Data

Nov. 22, 1991 [DE] Fed. Rep. of Germany ....... 4138408

[51] Int. Cl.$^5$ ............. C08F 8/40; C08J 3/24; C08K 5/5373; C08K 5/15
[52] U.S. Cl. .................. 525/340; 524/530; 524/916; 525/330.4; 525/329.8; 525/326.6; 525/287; 525/193; 526/278
[58] Field of Search ............ 526/278; 525/340, 330.4, 525/329.8, 287, 193; 524/530, 916

[56] References Cited

U.S. PATENT DOCUMENTS 4,927,248  5/1990  Sakakibara et al. ................. 350/452
5,011,892  4/1991  Engelhardt et al. ................. 525/404

FOREIGN PATENT DOCUMENTS 0481370  4/1992  European Pat. Off. .
3911433  10/1989  Fed. Rep. of Germany .
3911443  10/1989  Fed. Rep. of Germany .

OTHER PUBLICATIONS

*Chem. Abstracts;* 99: 45968q (1983), p. 486 Brainiw et al. (Russ).
*Chem. Abstracts* 68: 94873p (1964) Bloechl CDE 1,254,150-B).

Primary Examiner—Paul R. Michl
Assistant Examiner—Andrew E. C. Merriam
Attorney, Agent, or Firm—Connolly and Hutz

[57] ABSTRACT

The present invention relates to a hydrophilic, highly swellable hydrogel based on (co)polymerized hydrophilic monomers or based on graft (co)polymers, characterized in that it has been surface-modified by means of a mixture of A) one or more diglycidyl phosphonates and
B) one or more other reactive compounds which are capable of reacting with the functional groups in the polymer, to a process for the preparation thereof, to the use thereof, and to diglycidyl phosphonate-containing crosslinking agent mixtures.

23 Claims, No Drawings

HYDROPHILIC, HIGHLY SWELLABLE HYDROGELS

The present invention relates to hydrophilic, highly swellable hydrogels which have been surface-modified by means of a diglycidyl phosphonate-containing crosslinking agent mixture, to a process for the preparation thereof, to the use thereof and to diglycidyl phosphonate-containing crosslinking agent mixtures.

Hydrophilic hydrogels which can be obtained by polymerization of olefinically unsaturated acids, such as, for example, acrylic acid, methacrylic acid, acrylamidopropane -sulphonic acid, etc., in the presence of small amounts of polyolefinically unsaturated compounds have already been disclosed and are described, for example, in U.S. Pat. No. 4,057,521, U.S. Pat. No. 4,062,817, U.S. Pat. No. 4,525,527, U.S. Pat. No. 4,286,082, U.S. Pat. No. 4,340,706 and U.S. Pat. No. 4,295,987.

Furthermore, hydrophilic hydrogels which can be obtained by graft copolymerization of olefinically unsaturated acids on various matrices, such as, for example, polysaccharides, polyalkylene oxides, and the derivatives thereof, have also been disclosed (for example U.S. Pat. No. 5,011,892, U.S. Pat. No. 4,076,663 and U.S. Pat. No. 4,931,497).

Said hydrogels are distinguished by a high absorption capacity for water and aqueous solutions and are therefore preferably used as absorbents in hygiene articles.

It has already been disclosed that the properties of these hydrogels can be modified by surface treatment with certain substances.

For example, modifications by treatment with cationic polymers and polyamines (U.S. Pat. No. 4,824,901), with polyvalent metal cations (U.S. Pat. No. 5,002,986 and U.S. Pat. No. 4,771,105), with inorganic additives (U.S. Pat. No. 4,500,670), with alkoxysilyl compounds (EP-A 415 183 and EP-A 195 406) and with further substances, such as polyhydroxyl compounds, polyoxazolines, polyglycidyl ethers, etc. (EP-A 372 981, EP-A 317 106, U.S. Pat. No. 4,666,983 and U.S. Pat. No. 4,734,478), have been disclosed.

These modifications allow improved properties of the hydrogels with respect to mechanical stability and water-absorption rate to be achieved.

By contrast, the object of the present invention is to provide hydrogels having improved properties with respect to mechanical stability and water-retention capacity of the swollen particles.

This object is achieved by a hydrophilic, highly swellable hydrogel based on (co)polymerized hydrophilic monomers or based on graft (co)polymers, characterized in that it has been surface-modified by means of a mixture of A) one or more diglycidyl phosphonates of the general formula I

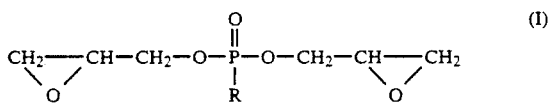

in which R is alkyl, alkenyl or aryl, each of which is optionally substituted and B) one or more other reactive compounds which are capable of reacting with the functional groups in the polymer.

The hydrophilic, highly swellable hydrogel according to the invention has preferably been surface-modified by means of a mixture of A) one or more diglycidyl phosphonates of the general formula I

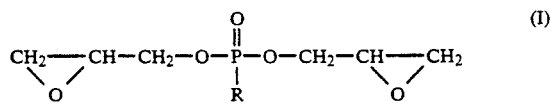

in which R is $(C_1-C_{18})$-alkyl; $(C_3-C_8)$-cycloalkyl; a group of the general formula II

in which $R^1$ and $R^2$, independently of one another are hydrogen or $(C_1-C_4)$-alkyl; or a group of the general formula III

in which $R^3$ is hydrogen, halogen or $(C_1-C_4)$-alkyl, and

B) one or more (poly)glycidyl ethers and/or one or more alkoxysilyl compounds and/or one or more polyaziridines and/or one or more polyamines and/or one or more polyamidoamines.

Alkyl groups representing R, $R^1$, R2 or $R^3$ may be straight-chain or branched.

$(C_1-C_{18})$-alkyl representing R is in particular methyl, ethyl, n-propyl, i-propyl, n-butyl, i-butyl, n-pentyl, i-pentyl, n-hexyl, i-hexyl, decyl or stearyl, but $(C_1-C_3)$-alkyl is particularly preferred.

A particularly preferred $(C_3-C_8)$-cycloalkyl is cyclohexyl.

$(C_1-C_4)$-alkyl representing $R^1$ or $R^2$ is particularly preferably methyl. However, $R^1$ and $R^2$ are very particularly preferably hydrogen.

The radical $R^3$ may be in the 2-, 3- or 4-position with respect to the carbon-phosphorus bond.

$(C_1-C_4)$-alkyl representing $R^3$ is in particular methyl, ethyl, n-propyl, i-propyl, n-butyl, i-butyl or tert.-butyl. Halogen representing $R^3$ is in particular fluorine, chlorine, bromine or iodine.

$R^3$ is particularly preferably methyl or chlorine, very particularly preferably hydrogen.

Particularly preferred compounds of the general formula I are diglycidyl methylphosphonate, diglycidyl n-propylphosphonate, diglycidyl stearylphosphonate and diglycidyl decanephosphonate.

Preferred (poly)glycidyl ethers are monoethylene glycol diglycidyl ether, polyethylene glycol diglycidyl ether, in particular nonethylene glycol diglycidyl ether, monopropylene glycol diglycidyl ether and polypropylene glycol diglycidyl ether.

Preferred alkoxysilyl compounds are aminoalkylalkoxy -silanes, such as, for example, 3-aminopropyltriethoxysilane, trimethoxysilylpropyldiethylenetriamine, N-aminoethylamino -propyltrimethoxysilane and aminoethylaminomethylphenethyltri -methoxysilane, and glycidylalkoxysilanes, such as, for example, 3-glycidyloxypropyltrimethoxysilane.

Preferred polyaziridines are adduction compounds of aziridine with polyunsaturated components, for example tri -methylolpropane tri[3-(1-aziridinyl)propionate].

A preferred polyamine is polyethylenimine.

Preferred polyamidoamines are condensates made from adipic acid and polyamines, such as, for example, diethylenetriamine.

The ratio between the compound(s) of the general formula I and the compound(s) as in B) may vary within broad limits. The proportion of the compound as in B) is preferably between 0.5 and 90% by weight, particularly preferably between 1 and 60% by weight.

If more than one compound of the general formula I is employed, the ratio by weight thereof is entirely unimportant. The same applies if more than one compound as in B) is employed.

In the hydrogels according to the invention, the proportion of the mixture of compound(s) of the general formula I and compound(s) as in B) is preferably from 0.01 to 10% by weight, particularly preferably from 0.05 to 3% by weight.

The polymers made from (co)polymerized, hydrophilic monomers or graft (co)polymers on which the hydrogels according to the invention are based are known and are described, for example, in the above-cited references.

Preference is given to polymers made from hydrophilic monomers, such as, for example, acrylic acid, methacrylic acid, crotonic acid, 2-acrylamido-2-methylpropanesulphonic acid and -phosphonic acid, vinylphosphonic acid, vinylphosphonic acid monoesters, salts thereof, acrylamide,. N-vinylamides or mixtures thereof, it being possible for all or some of the acid groups to be in neutralized form.

Preference is also given to graft polymers based on starch, cellulose or cellulose derivatives, and to the graft polymers described in U.S. Pat. No. 4,931,497 and U.S. Pat. No. 5,011,892.

The polymers or graft polymers on which the hydrogels according to the invention are based may also have already been crosslinked by means of suitable crosslinking agents, such as, for example, methylenebisacrylamide, bisacrylamidoacetic acid, esters of alkenylphosphonic or -phosphinic acids, trimethylolpropane tri(meth)acrylate or tetraallyloxyethane.

The hydrogels according to the invention preferably have an average particle size distribution of from 20 to 1,000 μm, particularly preferably from 100 to 1,000 μm.

In addition, preference is given to hydrogels according to the invention in which the proportion by weight in the particle size range from 400 to 1,680 μm is greater than 50%.

The hydrogels according to the invention can be prepared by treating the polymers made from (co)-polymerized hydrophilic monomers or the graft (co)-polymers in solid form, preferably in powder form, having a particle size distribution of between 20 and 1,000 μm, preferably between 100 and 850 μm, in a mixer with a mixture of one or more compounds of the general formula I and one or more compounds as in B).

Examples of suitable mixers are Patterson-Kelly mixers, DRAIS turbulence mixers, Lödige mixers, screw mixers, plate mixers and fluidised-bed mixers.

The process is preferably carried out in the temperature range between 0° and 200° C., preferably from 80° to 180° C. It is preferred to prewarm the polymer or graft polymer to be modified to a temperature of from 40° to 100° C. before carrying out the process. In a preferred embodiment, the components are mixed in a conventional, heatable mixer at a temperature between 20° and 60° C. and then, in order to accelerate the reaction in the region close to the surface, heated to a temperature between 80° and 200° C., preferably from 80° to 150° C. In a further preferred embodiment, this heat-treatment step is carried out in a downstream drier for a period of 10 minutes to 6 hours, during which elimination products which may be produced during the reaction and any solvent components which had previously been added can be removed.

The mixtures of components A) and B) can be employed either in solid form or in the form of solutions.

Preferred solvents are water, alcohols, esters, ketones, ethers and hydrocarbons, and mixtures of these components, having boiling points of up to 200° C., preferably up to 150° C.

It is also possible to first modify the polymers made from (co)polymerized hydrophilic monomers or the graft (co)polymers by means of component A and subsequently by means of component B.

The above invention also relates to crosslinking agent mixtures comprising

A) one or more diglycidyl phosphonates of the general formula I

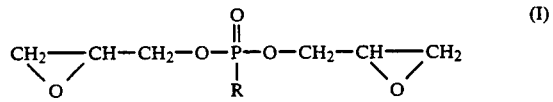

in which R is alkyl, alkenyl or aryl, each of which is optionally substituted, and B) one or more other reactive compounds which are capable of reacting with the functional groups of the polymer to be crosslinked.

Preferred crosslinking agent mixtures comprise

A) one or more diglycidyl phosphonates of the general formula I

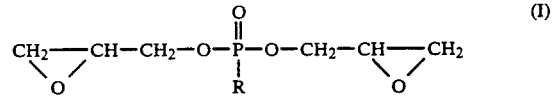

in which R is $(C_1-C_{18})$-alkyl; $(C_3-C_8)$-cycloalkyl; a group of the general formula II

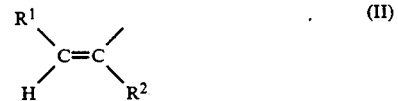

in which $R^1$ and $R^2$, independently of one another, are hydrogen or $(C_1-C_4)$-alkyl; or a group of the general formula III

in which $R^3$ is hydrogen, halogen or ($C_1$–$C_4$)-alkyl, and
B) one or more (poly)glycidyl ethers and/or one or more alkoxysilyl compounds and/or one or more polyaziridines and/or one or more-polyamines and/or one or more polyamidoamines.

Further preferred embodiments of the crosslinking agent mixtures according to the invention, with respect to components A) and B), correspond to the preferred statements already made above.

The crosslinking agent mixtures according to the invention can be obtained by simply mixing the components.

The compounds of the general formula I can be prepared by known methods.

Thus, for example, U.S. Pat. No. 2,856,369 describes the reaction of diallyl phosphonates with peracids to give the corresponding diglycidyl phosphonates of the general formula I, and Doklady Akad. SSSR, 155 (1964) 1137 describes the reaction of phosphonus acid dichlorides with glycide in the presence of a base to give the corresponding diglycidyl phosphonates, which may themselves be converted into compounds of the general formula I using oxidants such as $N_{20}O_4$.

The compounds of the general formula I are preferably prepared by reacting the corresponding phosphonic acid dichlorides with glycide in the presence of a base. The base is necessary to scavange the HCl which is formed in the reaction of phosphonic acid dichloride with glycide and results in side and secondary reactions. Zh. Obshch. Khim 116 (1984) 2404 recommends NaH as base, but nitrogen-containing bases are more frequently used. These include, in particular, tertiary amines, such as trimethylamine, triethylamine, tripropylamine or tributylamine. U.S. Pat. No. 2,856,369 also recommends the use of pyridine. Preference is given to trialkylamines, particularly preferably triethylamine.

Preferred solvents for these reactions are diethyl ether, methyl tert.-butyl ether, benzene, toluene or xylenes, but other inert solvents and mixtures of different solvents are also suitable. Solvents which are particularly suitable for industrial purposes are those such as methyl tert.-butyl ether, tetrahydrofuran, toluene or xylenes, and mixtures thereof, toluene being particularly preferred.

The reactants and the necessary base are usually employed in stoichiometric amounts, but excesses of the base and/or glycide may also be advantageous. Reasons for the amounts preferably used in each case may be of a process-related or application-related nature. Application-related reasons include, inter alia, purity criteria, such as: colour, highest possible contents of active substance, lowest possible contents of byproducts, lowest possible contents of starting compounds and lowest possible contents of hydrolysable and/or ionogenic chlorine. In the latter case, a slight, 1–20 mol %, preferably 1–5 mol %, excess of amine is frequently advisable.

For the reaction, a mixture of glycide and base is usually introduced into the solvent used, and the phosphonic acid dichloride is added dropwise, either as it is or dissolved in one of the solvents described. Other procedures are also possible. For example, the glycide can be added dropwise to a mixture of the amine and the phosphonic acid dichloride. Continuous procedures are also possible. To this end, for example, streams of glycide and amine are combined with a stream of the corresponding phosphonic acid dichloride and reacted in this way. One or both streams then contain the requisite solvent, which is necessary to prevent blockages of the pipelines due to amine hydrochloride precipitating out.

When the reaction is complete, the precipitated amine hydrochloride is usually separated off, for example by filtration or centrifugation. If a solvent-free product is required, the solvent is subsequently removed by distillation, if necessary under reduced pressure. The crude product obtained in this way can be further purified by distillation under reduced pressure either from the still, but preferably in a continuous manner by distillation in a thin-film or short-path evaporator.

The components B used are known and can be prepared by methods which are known to a person skilled in the art and are described in the relevant literature. Some of them are also commercially available products.

The hydrophilic, highly swellable hydrogels according to the invention are highly suitable as absorbents for water and aqueous solutions and can be used in particular in the production of hygiene articles, such as nappies, sanitary towels, tampons and other absorptive products. It is particularly advantageous here that the polymer particles in the swollen state do not tend to stick together even under mechanical load.

The production of hygiene articles, in particular nappies, using hydrogels is known per se to a person skilled in the art and is described in the literature.

EXAMPLE 1 a) Preparation of the Polymer to be Modified 5,240 g of demineralised water are introduced into a polyethylene vessel which is well insulated by foamed plastic material and has a capacity of 10 l, 1,505 g of sodium bicarbonate are suspended therein, and 1,980 g of acrylic acid are metered in slowly so that the reaction solution is prevented from foaming over, the solution being cooled to a temperature of from about 5° to 3° C. A mixture of 20 g of trimethylolpropane triacrylate in 16 g of a polyglycol ether based on a synthetic $C_{12}$–$C_{15}$-oxo alcohol containing about 13 ethylene oxide units, and 10 g of a sodium diisooctylsulphosuccinate is then added. At a temperature of 4° C., the initiators, a redox system comprising 2.2 g of 2,2'-azobisamidinopropane dihydrochloride, dissolved in 20 g of demineralised water, 6 g of potassium peroxodisulphate, dissolved in 170 g of demineralised water, and 0.4 g of ascorbic acid, dissolved in 120 g of demineralised water, are added successively, and the mixture is stirred vigorously. The reaction solution is then left to stand without stirring, during which time a solid gel forms due to commencing polymerization, in the course of which the temperature increases to about 85° C. The gel is subsequently comminuted mechanically, dried at temperatures above 80° C. and ground, and the fraction between 100 and 850 μm is removed by screening. A product is obtained which is characterized by the following physical data, all measured in 0.9% NaCl:

| | |
|---|---|
| Absorption under load (20 g/cm$^2$ - 1 hour) | 9.4 g/g |
| Absorption (teabag, drip test - 10/10 min.) | 47 g/g |
| Centrifuge retention (teabag - 10/3 min.) | 36 g/g |
| Extractable content (16 hours) | 17.4% | b) Surface Modification 6 kg of polymer powder, prepared as described in Example 1a), are introduced into a PETTERSON & KELLY mixer with a capacity of 10 l. A solution of 6 g of diglycidyl methylphosphonate, 6 g of nonaethylene glycol diglycidyl ether and 228 g of water is sprayed in in the course of 7 minutes with mixing, and the components are mixed for a further 1 minute. The product is subsequently heated at 130° C. for 30 minutes in a drying cabinet. It is characterized by the following physical data, all measured in 0.9% NaCl:

| | |
|---|---|
| Absorption under load (20 g/cm² - 1 hour) | 30.6 g/g |
| Absorption (teabag, drip test - 10/10 min.) | 46 g/g |
| Centrifuge retention (teabag - 10/3 min.) | 34 g/g |
| Extractable content (16 hours) | 16.6% |

EXAMPLE 2 a) Preparation of the Polymer to be Modified 3,615 g of demineralised water, cooled to 15° C., are introduced under adiabatic conditions into a 5 l cylindrical wide-neck reaction flask, and 490 g of a starch solution which has been boiled and likewise cooled to 15° C. and comprises 45 g of maize starch and 445 g of demineralised water, 850 g of acrylic acid and 4.25 g of tetraallyloxyethane are dissolved therein. Nitrogen (about 2 l/min.) is passed into the monomer solution in order to reduce the oxygen content. 64 g of a 4% strength aqueous solution of 2,2'-azobis(2-amidinopropane) dihydrochloride are added at an O₂ content of about 1.5 ppm, 12 g of a 0.75% strength H₂O₂ solution are added after further N₂ has been passed in and at an O₂ content of about 1.3 ppm, and finally 12 g of a 0.15% strength ascorbic acid solution are added at an O₂ content of <1.0 ppm. Commencing polymerization, during the course of which the temperature increases to about 65° C., results in the formation of a solid gel, which is subsequently comminuted mechanically. 1,000 g of the comminuted gel are treated with 346 g of 27% strength sodium hydroxide solution (degree of neutralization of the acrylic acid =70 mol %), and the mixture is thoroughly kneaded three times, subsequently dried in a thin layer at temperatures above 150° C. and ground, and, if desired, the fraction between 50 and 850 μm is removed by screening.

A product is obtained which is characterized by the following physical data, all measured in 0.9% NaCl:

| | |
|---|---|
| Absorption under load (20 g/cm² - 1 hour) | 15 g/g |
| Absorption (teabag, drip test - 10/10 min.) | 50 g/g |
| Centrifuge retention (teabag - 10/3 min.) | 36 g/g |
| Extractable content (16 hours) | 7% | b) Surface Modification 35 kg of polymer powder having a bulk density of 0.46 g/cm3, prepared as described in Example 2a), are introduced into a LÖDIGE plough mixer with a capacity of 100 l and heated to 80° C. When the product temperature has been reached, a solution of 87.5 g of diglycidyl propylphosphonate, 87.5 g of a glycidylorganofunctional polydimethylsiloxane (TEGOMER® E-SI 7235/commercial product from TH. GOLDSCHMIDT AG) and 425 g of isopropanol and 50 g of water are sprayed in over the course of 5 to 10 minutes. The mixture is heated to a product temperature of 100° C. in order to distil the solvent off again, and is subsequently cooled down again directly.

A product is obtained which is characterized by the following physical data, all measured in 0.9% NaCl:

| | |
|---|---|
| Absorption under load (20 g/cm² - 1 hour) | 27 g/g |
| Absorption (teabag, drip test - 10/10 min.) | 61 g/g |
| Centrifuge retention (teabag - 10/3 min.) | 40 g/g |
| Extractable content (16 hours) | 4.5% |

EXAMPLE 3 a) Preparation of the Polymer to be Modified

In accordance with U.S. Pat. No. 4,931,497, 5,310 g of demineralised water are introduced into a polyethylene vessel with a capacity of 10 l which is well insulated by foamed plastic material, 1,219 g of sodium bicarbonate are suspended therein, and 1,972 g of acrylic acid are metered in slowly at such a rate that the reaction solution is prevented of foaming over, the solution being cooled to a temperature about 5° to 3° C. A slurry of 4 g of methylenebisacrylamide in 100 g of water and 24 g of the product of the reaction of 1 mol of polyethylene glycol having a mean molecular weight of 300 and 1.98 mol of maleic anhydride are then added. At a temperature of 4° C., the initiators, a redox system comprising 2.2 g of 2,2'-azobisamidinopropane dihydrochloride, dissolved in 20 g of demineralised water, 6 g of potassium peroxodisulphate, dissolved in 175 g of demineralised water, and 0.4 g of ascorbic acid, dissolved in 120 g of demineralised water, are added successively, and the mixture is stirred vigorously. The reaction solution is then left to stand without stirring, a solid gel forming due to commencing polymerization, during the course of which the temperature increases to about 85° C. This gel is subsequently comminuted mechanically, dried at temperatures above 80° C., and ground, and the fraction between 100 and 630 μm is removed by screening.

A product is obtained which is characterized by the following physical data, all measured in 0.9% NaCl:

| | |
|---|---|
| Absorption under load (20 g/cm² - 1 hour) | 8.5 g/g |
| Absorption (teabag, drip test - 10/10 min.) | 46 g/g |
| Centrifuge retention (teabag - 10/3 min.) | 32 g/g |
| Extractable content (16 hours) | 6.5% | b) Surface Modification 6 kg of polymer powder, prepared as described in Example 3a), are introduced into a PETTERSON & KELLY mixer with a capacity of 10 l. A solution of 1.2 g of diglycidyl n-propylphosphonate, 10.8 g of monoethylene glycol diglycidyl ether and 228 g of water is sprayed in over the course of 5 minutes with mixing, and the components are mixed for a further 1 minute. The product is subsequently heated at 130° C. for 30 minutes in a drying cabinet. It is characterized by the following physical data, all measured in 0.9% NaCl:

| | |
|---|---|
| Absorption under load (20 g/cm² - 1 hour) | 24.9 g/g |
| Absorption (teabag, drip test - 10/10 min.) | 45 g/g |
| Centrifuge retention (teabag - 10/3 min.) | 38 g/g |
| Extractable content (16 hours) | 6.8% |

EXAMPLE 4

635 g of cyclohexane are introduced into a 2 l polymerization flask and warmed to from 40° to 45° C. with stirring; 3.5 g of ethylcellulose (type CN 200 from HERCULES, USA) are then added. The mixture is heated to the reflux temperature while a gentle stream of $N_2$ is passed in. After the mixture has refluxed for 25 minutes, a partially neutralized acrylic acid solution which has been cooled to room temperature and comprises 175 g of water, 230 g of acrylic acid, 258 g of 50% strength potassium hydroxide solution, blended with a solution of 20 g of water, 0.3 g of ethylenediaminetetraacetic acid, 0.1 g of $Na_2S_2O_8$ and 0.2 g of 4,4'-azobis-4-cyanovaleric acid is metered in over the course of 90 minutes by means of a metering pump. The reflux condenser is then replaced by a water separator, and the water is removed by azeotropic distillation. After the removal of the water by azeotropic distillation has commenced, an emulsion comprising 15 g of cyclohexane, 0.5 g of water, 0.45 g of diglycidyl stearylphosphonate, 0.05 g of ethylene glycol diglycidyl ether and 0.4 g of a sorbitan monolaurate is added. 260 g of water are removed by distillation, the solvent is separated from the polymer by filtration, the polymer is then dried for 2 hours at 105° C. in a drying cabinet, and the polymer particles differing from the standard in the particle size spectrum are, if necessary, removed by screening. A product is obtained which is characterized by the following physical data, all measured in 0.9% NaCl using the particle size fraction from 0.3 to 0.4 mm:

| | |
|---|---|
| Absorption under load (20 g/cm² - 1 hour) | 27 g/g |
| Absorption (teabag, drip test - 10/10 min.) | 46 g/g |
| Centrifuge retention (teabag - 10/3 min.) | 32 g/g |
| Extractable content (16 hours) | 12% |

In order to characterize the hydrogels according to the invention, the absorption under load (AUL), the free absorption (FSC), the centrifuge retention (CR) and the modulus of elasticity G' were measured for the examples below.

The absorption under load (20 g/cm²) is determined by the method described in EP 0 339 461, page 7: the hydrogel sample of known weight is introduced into a cylinder with screen base, and the powder is loaded by means of a plunger which exerts a pressure of 20 g/cm². The cylinder is subsequently placed on a demand absorbency tester (DAT), where the superabsorber is allowed to absorb 0.9% strength NaCl solution for one hour.

The free absorption and the centrifuge retention are determined using the teabag method and as the mean of two measurements: About 0.2 g of hydrogel are welded into a teabag and dipped in 0.9% strength NaCl solution for 10 minutes. In order to determine the absorption, the teabag is then suspended diagonally for 10 minutes and subsequently weighed. In order to determine the retention, the teabag, after immersion, is centrifuged in a centrifuge (23 cm diameter, 1,400 rpm) for 3 minutes and weighed. The blank value is determined using a teabag without hydrogel:

$$\text{Absorption/retention} = \frac{\text{final weight} - \text{blank weight}}{\text{initial weight}} \text{ (g/g)}$$

The modulus of elasticity is measured using a Carri-Med-Stress rheometer having a plate/plate configuration. To determine the modulus of elasticity, 1 g of hydrogel is allowed to swell in 60 g of 0.9% strength NaCl solution for 24 hours, and the storage modulus is subsequently measured on this swollen gel as a function of the shear stress at a frequency of 1Hz. The plateau value is given as the modulus of elasticity G'.

EXAMPLES 5-32 a) Preparation of the Polymer to be Modified

The procedure is as in Example 2a, with the exception that, instead of 4.25 g, only 2.5 g of tetraallyloxyethane are employed. The fraction from 100–850 μm is removed from the dried and ground product by screening. The physical data are shown in Table 1.

b) Surface Modification

Each 100 g of powder from a) are mixed with vigorous stirring in each case with 10 g of a crosslinking agent solution containing components A and B, and the mixture is subsequently heated for 2 hours in an oven thermostated at 120° C. After cooling, the abovementioned measurements are determined, and are given in Table 1.

The following abbreviations are used:
IPA: isopropyl alcohol
A1: diglycidyl n-propylphosphonate
A2: diglycidyl decylphosphonate
A3: diglycidyl phenylphosphonate
A4: diglycidyl stearylphosphonate
B1: monoethylene glycol diglycidyl ether, epoxy equivalent (g/eq) =112
B2: nonaethylene glycol diglycidyl ether, epoxy equivalent (g/eq) =276
B3: glycidyl-organofunctional polydixnethylsiloxane having a comb structure, epoxy side groups, epoxy equivalent (g/eq) =500–600
B4: glycidyl-organofunctional polydimethylsiloxane having a comb structure, epoxy side groups, epoxy equivalent (g/eq) =1,000–1,200
B5: α,ω-glycidyl-functional polydimethylsiloxane, epoxy terminal groups, epoxy equivalent (g/eq) =500–630
B6: α,ω-glycidyl-functional polydimethylsiloxane, epoxy terminal groups, epoxy equivalent (g/eq) =1,100–1,230

TABLE 1

| Example | Crosslinking agent | | | | Crosslinking agent solution | AUL (g/g) | FSC (g/g) | CR (g/g) | EM (N/m²) |
| | Component A | Amount (% by wt) | Component B | Amount (% by wt) | | | | | |
|---|---|---|---|---|---|---|---|---|---|
| 5a | — | — | — | — | — | 13.8 | 63 | 42 | 150 |
| comparison | — | — | — | — | IPA/H₂O 50/50 | 13.9 | 62 | 42 | 158 |
| 5 | A1 | 0.25 | B1 | 0.25 | IPA/H₂O 50/50 | 32.8 | 60 | 33 | 745 |
| 6 | A1 | 0.25 | B1 | 2.25 | IPA/H₂O 50/50 | 31.8 | 61 | 34 | 710 |
| 7 | A1 | 1.00 | B1 | 1.00 | IPA/H₂O 50/50 | 33.0 | 59 | 30 | 810 |
| 8 | A1 | 2.50 | B1 | 0.25 | IPA/H₂O 50/50 | 32.2 | 60 | 31 | 850 |
| 9 | A1 | 2.50 | B1 | 2.50 | IPA/H₂O 50/50 | 32.0 | 59 | 31 | 860 |
| 10 | A1 | 0.25 | B2 | 0.25 | IPA/H₂O 50/50 | 32.4 | 62 | 33 | 680 |
| 11 | A1 | 0.25 | B2 | 2.25 | IPA/H₂O 50/50 | 30.1 | 58 | 32 | 735 |

TABLE 1-continued

| Example | Component A | Crosslinking agent Amount (% by wt) | Component B | Amount (% by wt) | Crosslinking agent solution | AUL (g/g) | FSC (g/g) | CR (g/g) | EM (N/m²) |
|---|---|---|---|---|---|---|---|---|---|
| 12 | A1 | 1.00 | B2 | 1.00 | IPA/H$_2$O 50/50 | 29.3 | 60 | 32 | 675 |
| 13 | A1 | 2.50 | B2 | 0.25 | IPA/H$_2$O 50/50 | 28.8 | 60 | 35 | 645 |
| 14 | A1 | 2.50 | B2 | 2.50 | IPA/H$_2$O 50/50 | 31.7 | 57 | 34 | 710 |
| 12 | A2 | 1.00 | B2 | 1.00 | IPA/H$_2$O 50/50 | 32.0 | 59 | 36 | 705 |
| 16 | A3 | 1.00 | B2 | 1.00 | IPA/H$_2$O 50/50 | 31.8 | 58 | 35 | 720 |
| 17 | A4/A1 | 0.01/0.01 | B1 | 0.15 | IPA/H$_2$O 50/50 | 26.4 | 59 | 36 | 480 |
| 18 | A1 | 0.25 | B3 | 0.25 | IPA/H$_2$O 70/30 | 25.2 | 61 | 40 | 525 |
| 19 | A1 | 0.25 | B3 | 2.25 | IPA/H$_2$O 85/15 | 15.1 | 60 | 40 | 405 |
| 20 | A1 | 2.50 | B3 | 2.50 | IPA/H$_2$O 90/10 | 15.9 | 59 | 35 | 400 |
| 21 | A1 | 0.25 | B4 | 0.25 | IPA | 21.2 | 58 | 36 | 615 |
| 22 | A1 | 1.00 | B4 | 1.00 | IPA | 17.3 | 59 | 36 | 555 |
| 23 | A1 | 2.50 | B4 | 0.25 | IPA | 15.1 | 50 | 36 | 498 |
| 24 | A1 | 2.50 | B4 | 2.50 | IPA | 16.3 | 57 | 34 | 523 |
| 25 | A1 | 0.25 | B5 | 0.25 | IPA/H$_2$O 90/10 | 21.2 | 58 | 33 | 640 |
| 26 | A1 | 0.25 | B5 | 2.25 | IPA/H$_2$O 90/10 | 21.4 | 60 | 31 | 612 |
| 27 | A1 | 1.00 | B5 | 1.00 | IPA/H$_2$O 90/10 | 15.5 | 47 | 37 | 535 |
| 28 | A1 | 2.50 | B5 | 2.50 | IPA/H$_2$O 90/10 | 17.6 | 57 | 35 | 500 |
| 29 | A1 | 0.25 | B6 | 0.25 | IPA | 15.4 | 60 | 36 | 430 |
| 30 | A1 | 0.25 | B6 | 2.25 | IPA | 17.1 | 57 | 35 | 495 |
| 31 | A1 | 1.00 | B6 | 1.00 | IPA | 16.8 | 55 | 36 | 510 |
| 32 | A4 | 1.00 | B3/B5 | 2.00/7.00 | IPA | 26.3 | 48 | 32 | 920 |

EXAMPLES 33–67

Each 100 g of powder from Example 5a are mixed with vigorous stirring successively with in each case 5 g of a cross-linking agent solution containing component A and in each case 5 g of a crosslinking agent solution containing component B, and the mixture is subsequently heated for 2 hours in an oven thermostated at 120° C. After cooling, the abovementioned measurements are determined and are shown in Table 2.

The following additional abbreviations are used:
B7: 3-glycidyloxlrpropyl trimethoxysilane
B8: (aminoethylaminomethyl)phenylmethoxysilane
B9: 3-aminopropyltriethoxysilane
B10: trimethoxysilylpropyldiethylenetriamine
B11: commercially available polyamidoamine
B12: commercially available polyaziridine
B13: commercially available polyethyleneimine

TABLE 2

| Example | Component A | Crosslinking agent Amount (% by wt) | Component B | Amount (% by wt) | Crosslinking agent solution | AUL (g/g) | FSC (g/g) | CR (g/g) | EM (N/m²) |
|---|---|---|---|---|---|---|---|---|---|
| 33 | A1 | 0.25 | B7 | 0.25 | IPA/H$_2$O 50/50 | 33.2 | 62 | 33 | 810 |
| 34 | A1 | 0.25 | B7 | 2.25 | IPA/H$_2$O 50/50 | 25.7 | 60 | 34 | 695 |
| 35 | A1 | 1.00 | B7 | 1.00 | IPA/H$_2$O 50/50 | 30.6 | 60 | 34 | 731 |
| 36 | A1 | 2.50 | B7 | 0.25 | IPA/H$_2$O 50/50 | 22.6 | 63 | 36 | 683 |
| 37 | A1 | 2.50 | B7 | 2.50 | IPA/H$_2$O 50/50 | 21.3 | 59 | 36 | 680 |
| 38 | A1 | 0.25 | B8 | 0.25 | IPA/H$_2$O 75/25 | 32.8 | 61 | 35 | 680 |
| 39 | A1 | 0.25 | B8 | 2.25 | IPA/H$_2$O 75/25 | 31.2 | 58 | 34 | 735 |
| 40 | A1 | 1.00 | B8 | 1.00 | IPA/H$_2$O 75/25 | 29.8 | 57 | 33 | 675 |
| 41 | A1 | 2.50 | B8 | 0.25 | IPA/H$_2$O 75/25 | 29.3 | 51 | 28 | 645 |
| 42 | A1 | 2.50 | B8 | 2.50 | IPA/H$_2$O 75/25 | 30.7 | 46 | 27 | 710 |
| 43 | A1 | 0.25 | B9 | 0.25 | IPA/H$_2$O 75/25 | 32.7 | 60 | 32 | 722 |
| 44 | A1 | 0.25 | B9 | 2.25 | IPA/H$_2$O 75/25 | 28.4 | 57 | 32 | 614 |
| 45 | A1 | 1.00 | B9 | 1.00 | IPA/H$_2$O 75/25 | 30.4 | 54 | 29 | 654 |
| 46 | A1 | 2.50 | B9 | 0.25 | IPA/H$_2$O 75/25 | 30.3 | 53 | 28 | 670 |
| 47 | A1 | 2.50 | B9 | 2.50 | IPA/H$_2$O 75/25 | 30.4 | 52 | 28 | 655 |
| 48 | A1 | 0.25 | B10 | 0.25 | IPA/H$_2$O 75/25 | 26 | 65 | 34 | 525 |
| 49 | A1 | 0.25 | B10 | 2.25 | IPA/H$_2$O 75/25 | 19.6 | 64 | 34 | 512 |
| 50 | A1 | 1.00 | B10 | 1.00 | IPA/H$_2$O 75/25 | 28.5 | 57 | 33 | 680 |
| 51 | A1 | 2.50 | B10 | 0.25 | IPA/H$_2$O 75/25 | 30.5 | 56 | 31 | 653 |
| 52 | A1 | 2.50 | B10 | 2.50 | IPA/H$_2$O 75/25 | 30.5 | 46 | 30 | 624 |
| 53 | A1 | 0.25 | B11 | 0.25 | IPA/H$_2$O 75/25 | 31.5 | 54 | 31 | 615 |
| 54 | A1 | 0.25 | B11 | 2.25 | IPA/H$_2$O 75/25 | 30.1 | 59 | 30 | 555 |
| 55 | A1 | 1.00 | B11 | 1.00 | IPA/H$_2$O 75/25 | 29.8 | 57 | 29 | 500 |
| 56 | A1 | 2.50 | B11 | 0.25 | IPA/H$_2$O 75/25 | 25.5 | 45 | 24 | 523 |
| 57 | A1 | 2.50 | B11 | 2.50 | IPA/H$_2$O 75/25 | 26.9 | 48 | 24 | 540 |
| 58 | A1 | 0.25 | B12 | 0.25 | IPA/H$_2$O 75/25 | 30.5 | 55 | 29 | 678 |
| 59 | A1 | 0.25 | B12 | 2.25 | IPA/H$_2$O 75/25 | 28.2 | 58 | 30 | 610 |
| 60 | A1 | 1.00 | B12 | 1.00 | IPA/H$_2$O 75/25 | 28.8 | 48 | 26 | 535 |
| 61 | A1 | 2.50 | B12 | 0.25 | IPA/H$_2$O 75/25 | 28.3 | 44 | 25 | 500 |
| 62 | A1 | 2.50 | B12 | 2.50 | IPA/H$_2$O 75/25 | 29.3 | 46 | 27 | 531 |
| 63 | A1 | 0.25 | B13 | 0.25 | IPA/H$_2$O 75/25 | 31.8 | 57 | 34 | 778 |
| 64 | A1 | 0.25 | B13 | 2.25 | IPA/H$_2$O 75/25 | 27.9 | 51 | 34 | 614 |
| 65 | A1 | 1.00 | B13 | 1.00 | IPA/H$_2$O 75/25 | 29.7 | 46 | 30 | 675 |
| 66 | A1 | 2.50 | B13 | 0.25 | IPA/H$_2$O 75/25 | 30.4 | 64 | 29 | 715 |
| 67 | A1 | 2.50 | B13 | 2.50 | IPA/H$_2$O 75/25 | 27.8 | 55 | 26 | 625 |

We claim:

1. Hydrophilic, highly swellable hydrogel derived from hydrophilic monomers in (co)polymerized form or derived from graft (co)polymers, in which the hydrogel is further surface modified by means of a mixture of
   A) one or more diglycidyl phosphonates of general formula I

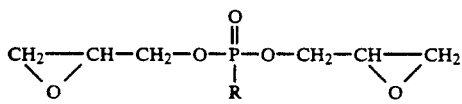

in which R is alkyl, alkenyl or aryl, each of which is optionally substituted, and
   B) one or more other reactive compounds which are capable of reacting with the functional groups in the polymer.

2. Hydrophilic, highly swellable hydrogel according to claim 1, wherein R is $(C_1-C_{18})$-alkyl; $(C_3-C_8)$-cycloalkyl; a group of the general formula II

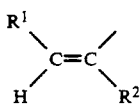

in which $R^1$ and $R^2$, independently of one another, are hydrogen or $(C_1-C_4)$-alkyl; or a group of the general formula III

in which $R^3$ is hydrogen, halogen or $(C_1-C_4)$-alkyl, and component B) is one or more (poly)glycidyl ethers and/or one or more alkoxysilyl compounds and/or one or more polyaziridines and/or one or more polyamines and/or one or more polyamidoamines.

3. Hydrophilic, highly swellable hydrogel according to claim 1, wherein R is selected from the group consisting of methyl, ethyl, n-propyl, i-propyl, n-butyl, i-butyl, n-pentyl, i-pentyl, n-hexyl, i-hexyl, decyl, stearyl and cyclohexyl.

4. Hydrophilic, highly swellable hydrogel according to claim 1, wherein $R_1$ or $R_2$ is methyl.

5. Hydrophilic, highly swellable hydrogel according to claim 1, wherein $R_3$ is in the 2-, 3- or 4-position with respect to the carbon-phosphorus bond.

6. Hydrophilic, highly swellable hydrogel according to claim 1, wherein $R_3$ is selected from the group consisting of methyl, ethyl, n-propyl, i-propyl, n-butyl, i-butyl, tert-butyl, fluorine, chlorine, bromine, iodine and hydrogen.

7. Hydrophilic, highly swellable hydrogel according to claim 1, wherein $R_3$ is selected from the group consisting of methyl, chlorine, and hydrogen.

8. Hydrophilic, highly swellable hydrogel according to claim 1, wherein the compounds of general formula I are selected from the group consisting of diglycidyl methylphosphonate, diglycidyl n-propylphosphonate, diglycidyl stearylphosphonate and diglycidyl decanephosphonate.

9. Hydrophilic, highly swellable hydrogel according to claim 2, wherein the (poly)glycidyl ethers are monoethylene glycol diglycidyl ether or polyethylene glycol diglycidyl ether.

10. Hydrophilic, highly swellable hydrogel according to claim 2, wherein the (poly)glycidyl ethers are nonethylene glycol diglycidyl ether, monopropylene glycol diglycidyl ether or polypropylene glycol diglycidyl ether.

11. Hydrophilic, highly swellable hydrogel according to claim 2, wherein the alkoxysilyl compounds are aminoalkylalkoxysilanes.

12. Hydrophilic, highly swellable hydrogel according to claim 11, wherein the aminoalkylalkoxysilanes are selected from the group consisting of 3-aminopropyltriethoxysilane, trimethoxysilyl -propyldiethylenetriamine, N-aminoethylaminopropyltrimethoxysilane, aminoethylaminomethylphenethyltrtmethoxysilane and glycidylalkoxysilanes.

13. Hydrophilic, highly swellable hydrogel according to claim 1, wherein the proportion of B) in the mixture of compound(s) of the general formula I and compound(s) as in B) Is from 0.5 to 90% by weight.

14. Hydrophilic, highly swellable hydrogel according to claim 1, wherein the proportion of B) in the mixture of compound(s) of the general formula I and compound(s) as in B) Is from 1 to 60% by weight.

15. Hydrophilic, highly swellable hydrogel according to claim 1, wherein the proportion of the mixture of compound(s) of the general formula I and compound(s) as in B) is from 0.01 to 10% by weight.

16. Hydrophilic, highly swellable hydrogel according to claim 1, wherein the proportion of the mixture of compound(s) of the general formula I and compound(s) as In B) is from 0.05 to 3% by weight.

17. An adsorbent for water and aqueous solutions comprising the hydrophilic, highly swellable hydrogel as claimed in claim 1.

18. Process for the preparation of a hydrophilic, highly swellable hydrogel according to claim 1, wherein the polymers made from (co)polymerized hydrophilic monomers or graft (co)polymers in solid form, having a particle size distribution of between about 20 and about 1,000 μm, are treated in a mixer with a mixture of one or more compounds of the general formula I and one or more compounds as in B).

19. Process for the preparation of a hydrophilic, highly swellable hydrogel according to claim 18, wherein the particle size distribution is between about 100 and about 850 μm.

20. Crosslinking agent mixture comprising
   A) one or more diglycidyl phosphonates of the general formula I

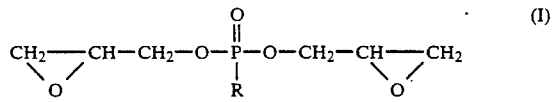

in which R is alkyl, alkenyl or aryl, each of which is optionally substituted, and
   B) one or more other reactive compounds which are capable of reacting with the functional groups of the polymer to be crosslinked.

21. Crosslinking agent mixture according to claim 20, comprising
   A) one or more diglycidyl phosphonates of the general formula I

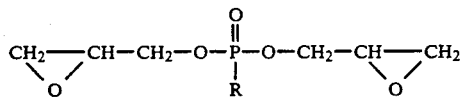 (I)

in which R is $(C_1-C_{18})$-alkyl; $(C_3-C_8)$-cycloalkyl; a group of the general formula II

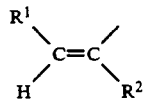 (II)

in which $R^1$ and $R^2$ independently of one another, are hydrogen or $(C_1-C_4)$-alkyl; or a group of the general formula III

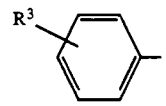 (III)

in which $R^3$ is hydrogen, halogen or $(C_1-C_4)$-alkyl, and

B) one or more (poly)glycidyl ethers and/or one or more alkoxysilyl compounds and/or one or more polyaziridines and/or one or more polyamines and/or one or more polyamidoamines.

22. A method for the production of hygiene articles comprising incorporating the hydrophilic, highly swellable hydrogel as claimed in claim 1 into said hygiene articles.

23. The surface modification of hydrophilic monomers in (co)polymerized for or of graft (co)polymers comprising reacting said polymers with the crosslinking agent mixture as claimed in claim 20.